US006849661B2

(12) United States Patent
Kelly et al.

(10) Patent No.: US 6,849,661 B2
(45) Date of Patent: Feb. 1, 2005

(54) TREATMENT OF ABNORMAL INCREASES IN GASTROINTESTINAL MOTILITY WITH (R)-VERAPAMIL

(75) Inventors: John Kelly, Dublin (IE); John Devane, Roscommon (IE); Ted G. Dinan, Cork (IE); P.W. Napoleon Keeling, Dublin (IE)

(73) Assignee: AGI Therapeutics, Ltd., Dublin (IE)

( * ) Notice: Subject to any disclaimer, the term of this patent is extended or adjusted under 35 U.S.C. 154(b) by 58 days.

(21) Appl. No.: 10/294,692

(22) Filed: Nov. 15, 2002

(65) Prior Publication Data

US 2004/0063784 A1 Apr. 1, 2004

Related U.S. Application Data

(63) Continuation-in-part of application No. 10/256,261, filed on Sep. 27, 2002, now abandoned.

(51) Int. Cl.[7] .............................................. A61K 31/275
(52) U.S. Cl. ...................................................... 514/523
(58) Field of Search ......................................... 514/523

(56) References Cited

U.S. PATENT DOCUMENTS

| | | | |
|---|---|---|---|
| 5,889,060 A | 3/1999 | Harding ...................... | 514/654 |
| 5,892,093 A | 4/1999 | Bannister et al. ........... | 558/354 |
| 5,910,601 A | 6/1999 | McCague et al. ........... | 558/354 |
| 5,932,246 A | 8/1999 | Harding et al. ............. | 424/451 |
| 5,955,500 A | 9/1999 | Longstreth et al. ......... | 514/523 |
| 6,190,691 B1 | 2/2001 | Mak ........................... | 424/449 |
| 6,267,980 B1 | 7/2001 | Gilbert et al. .............. | 424/424 |

FOREIGN PATENT DOCUMENTS

| | | | | |
|---|---|---|---|---|
| WO | WO 97/44025 | 11/1997 | ......... | A61K/31/275 |
| WO | WO 98/05321 | 2/1998 | ......... | A61K/31/275 |

OTHER PUBLICATIONS

Medline an 1999063874, Marvola et al, Eur. J. Pharmaceutical Sci. 1999 Feb 7(3) 259–67, abstract.*
Echizen et al. "The Effect of Dextro–, Levo–, and Racemic Verapamil on Atrioventricular Conduction in Humans," *American Heart Journal*, 109: 210–217, 1985.
Echizen et al., "Effects of D,L–Verapamil on Atrioventricular Conduction in Relation to Its Stereoselective First–Pass Metabolism," *Clinical Pharmacology& Therapeutics*, 38: 71–76, 1985.
Echizen et al., "Electrophysiologic Effects of Dextro– and Levo– Verapamil on Sinus Node and AV Node Function in Humans," *Journal of Cardiovascular Pharmacology*, 12(5): 543–546, 1988.
Kroemer et al., "Predictability of the in Vivo Metabolism of Verapamil from in Vitro Data: Contribution of Individual Metabolic Pathways and Stereoselective Aspects," *The Journal of Pharmacology and Experimental Therapeutics*, 260(3): 1052–1057, 1992.

Miwa et al., "Patients with Constipation–Predominant Irritable Bowel Syndrome (IBS) May Have Elevated Serotonin Concentrations in Colonic Mucosa as Compared with Diarrhea–Predominant Patients and Subjects with Normal Bowel Habits," *Digestion*, 63: 188–194, 2001.
Vogelgesang et al., "Stereoselective First–Pass Metabolism of Highly Cleared Drugs: Studies of the Bioavailability of L– and D–Verapamil Examined with a Stable Isotope Techique," *British Journal of Clinical Pharmacology*, 18: 733–740, 1984.
Co–pending U.S. Application No. 10/256,261, filed Sep. 27, 2002.
Ahlman et al., "Verapamil and Diarrhoea in the Carcinoid Syndrome– Clinical and Experimental Observations on Serotonin Release," *Br. J. Cancer*, 54:251–256, 1986.
Beubler et al., "Involvement of 5–Hydroxytrptamine, Prostaglandin E2, and Cyclic Adenosine Monophosphate in Cholera Toxin–Induced Fluid Secretion in the Small Intestine of the Rat In Vivo," *Gastroenterology*, 96: 368–76, 1989.
Borsari et al., "L'effet thérapeutique de L'anticalcique Vérapamil dans la Diarrhée Chronique," *Schweiz. Med. Wschr.*, 121:1238–1242, 1991 (English–language abstract included).
Byrne, "Verapamil in the Treatment of Irritable Bowel Syndrome," *J. Clin. Psy.*, 48:9, 1987.
Cox et al., "Effect of Antisecretory Drugs on Experimentally Induced Weanling Diarrhoea in Piglets," *Commun.*, 13(12): 159–70, 1989.
de Ponti et al., "Inhibitory Effects of Calcium Channel Blockers on Intestinal Motility in the Dog," *Eur. J. Pharmacol.*, 168(2): 133–44, 1989.
Donowitz et al., "$Ca^{2+}$Channel Blockers Stimulate Ileal and Colonic Water Absorption," *Gastroenterology*, 89(4):858–66, 1985.
Fabia et al., "Effect of Putative Phospholipase A2 Inhibitors on Acetic Acid–Induced Acute Colitis in the Rat," *Br. J. Surg.*, 80: 1199–1204, 1993.
Fedorak et al., "Verapamil Alters Eicosanoid Synthesis and Accelerates Healing During Experimental Colitis in Rats," *Gastroenterology*, 102: 1229–1235, 1992.
Floch, "Use of Verapamil in the Treatment of Diarrhea due to Microscopic Colitis," *J. Clin. Gastroenterol.*, 32(4): 283, 2001.

(List continued on next page.)

*Primary Examiner*—Rebecca Cook
(74) *Attorney, Agent, or Firm*—Finnegan, Henderson, Farabow, Garrett & Dunner, L.L.P.

(57) ABSTRACT

The present invention is directed to methods of treating, preventing, and/or managing abnormal increases in gastrointestinal motility, and intestinal conditions that cause the same. Such conditions include, but are not limited to, irritable bowel syndrome (IBS), infectious diseases of the small and large intestines, and symptoms of any of the foregoing. In particular, the present invention discloses methods of using enriched (R)-verapamil, as well as compositions and formulations containing the same.

29 Claims, 3 Drawing Sheets

OTHER PUBLICATIONS

Gertner et al,, Verapamil Inhibits In–Vitro Leucotriene B4 Release by Rectal Mucosa in Active Ulcerative Colitis, *Aliment. Pharmacol. Ther.*, 6: 163–68, 1992.

Goyal et al., Studies on the Mechanism of *Escherichia coli* Heat–Stble Enterotoxin–Induced Diarrhoea in Mice, *Biochemica et Biophysica Acta*, 925: 341–346, 1987.

Gullikson et al., "Inhibition of Intestinal Secretion in the Dog: A New Approach for the Management of Diarrheal States," *J. Pharmacol. Exp. Ther.*, 219: 591–97, 1981.

Hedner et al., "Calcium Channel Blockers: Spectrum of Side Effects and Drug Interactions," *Acta Pharmacol. Toxicol.*, 58(Suppl 2):119–30, 1986.

Homaidan et al., "Electrolyte Transport in Piglets Infected With Transmissable Gastroenteritis Virus," *Gastroenterology*, 101: 895–901, 1991.

Kanwar et al., "Calcium and Protein Kinase C Play an Important Role in *Campylobacter Jejuni*–induced changes in $Na^{+and}$ $Cl^-$ Transport in Rat Ileum In Vitro," *Biochemica et Biophysica Acta*, 1270: 179–192, 1995.

Khurana, et al., "Studies on the Mechanism of Salmonella Typhimurium Enterotoxin–Induced Diarrhoes," *Biochim. Biophys. Acta*, 1097(3):171–76, 1991.

Köksoy et al., "The Prophylactic Effects of Superoxide Dismutase, Catalase, Desferrioxamine, Verapamil, and Disulfiram in Experimental Colitis," *J. R. Coll. Surg. Edinb.*, 42: 27–30, 1997.

Krevsky et al., "Effect of Verapamil on Human Intestinal Transit," *Dig. Dis. Sci.*, 37(6):919–924, 1992.

Lee et al., "$Ca^{2+}$Channel Blockade by Verapamil Inhibits GMCs and Diarrhea During Small Intestinal Inflammation," *American J. Phys.*, 36: G785–94, 1997.

McCleod, "Verapamil Effective in Irritable Bowel Syndrome?" *Med. J. Aust.*, 2(3):119 (letter), 1983

Piascik, "Stereoselective and Nonstereoselective Inhibition Exhibited by the Enantiomers of Verapamil," *Can. J. Physiol. Pharmacol.*, 68(3):439–446, 1990.

Satoh et al., "Coronary Vasodilator and Cardiac Effects of Optical Isomers of Verapamil in the dog," *J. Cardio. Pharm.*, 2:309–318, 1980.

Scheidler et al., "Use of Verapamil for the Symptomatic Treatment of Microscopic Colitis," *J. Clin. Gastroenterol.*, 32: 351–352, 2001.

Simmonds et al., "Antioxidant Effects of Aminosalicylates and Potential New Drugs for Inflammatory Bowel Disease: Assessment in Cell–Free Systems and Inflamed Human Colorectal Biopsies," *Aliment. Pharmacol. Ther.*, 13: 363–372, 1999.

Subissi et al., "Effects of Spasmolytics on $K^+$–Induced Contraction of Rat Intestine In Vivo," *European J. Pharmacol.*, 96: 295–301, 1983.

Tabibian, "Successful Treatment of Refractory Post–Vagotomy Syndrome with Verapamil," *Am. J. Gastroenterol.*, 85: 328–29, 1990.

Thollander et al., "Dihydropyridine Calcium Channel Antagonists Disrupt Migrating Myoelectric Complexes and Counteract Intestinal Disorders Associated With Morphine Withdrawal Diarrhea," *Scand. J. Gastroenterol.*, 28: 137–144, 1993.

Thulin et al., "Side Effects of Calcium Channel Blockers," *Scand. J. Prim. Health Care Suppl.*, 1:81–84, 1990.

Camilleri et al., "Review Article: Irritable Bowel Syndrome," *Aliment. Pharmaco. Ther.*, 11(1): 3–15, 1997.

Cherukuri et al., "Verapamil in Resistant Diarrhoea Predominant Subtype of Irritable Bowel Syndrome (IBS)," *Gastroenterology*, 106(4) Suppl.: A478, 1994.

Freeman et al., "Verapamil Therapy for Persistent Antral Spasms in a Child," *Southern Medical Journal*, 89(5): 529–530, 1996.

Longstreth, "Verapamil a Chiral Challenge to the Pharmacoklnetic and Pharmacodynamic Assessment of Bioavailability and Bioequivalence," *Drug Stereochemistry*, 18: 315–336, 1993.

\* cited by examiner

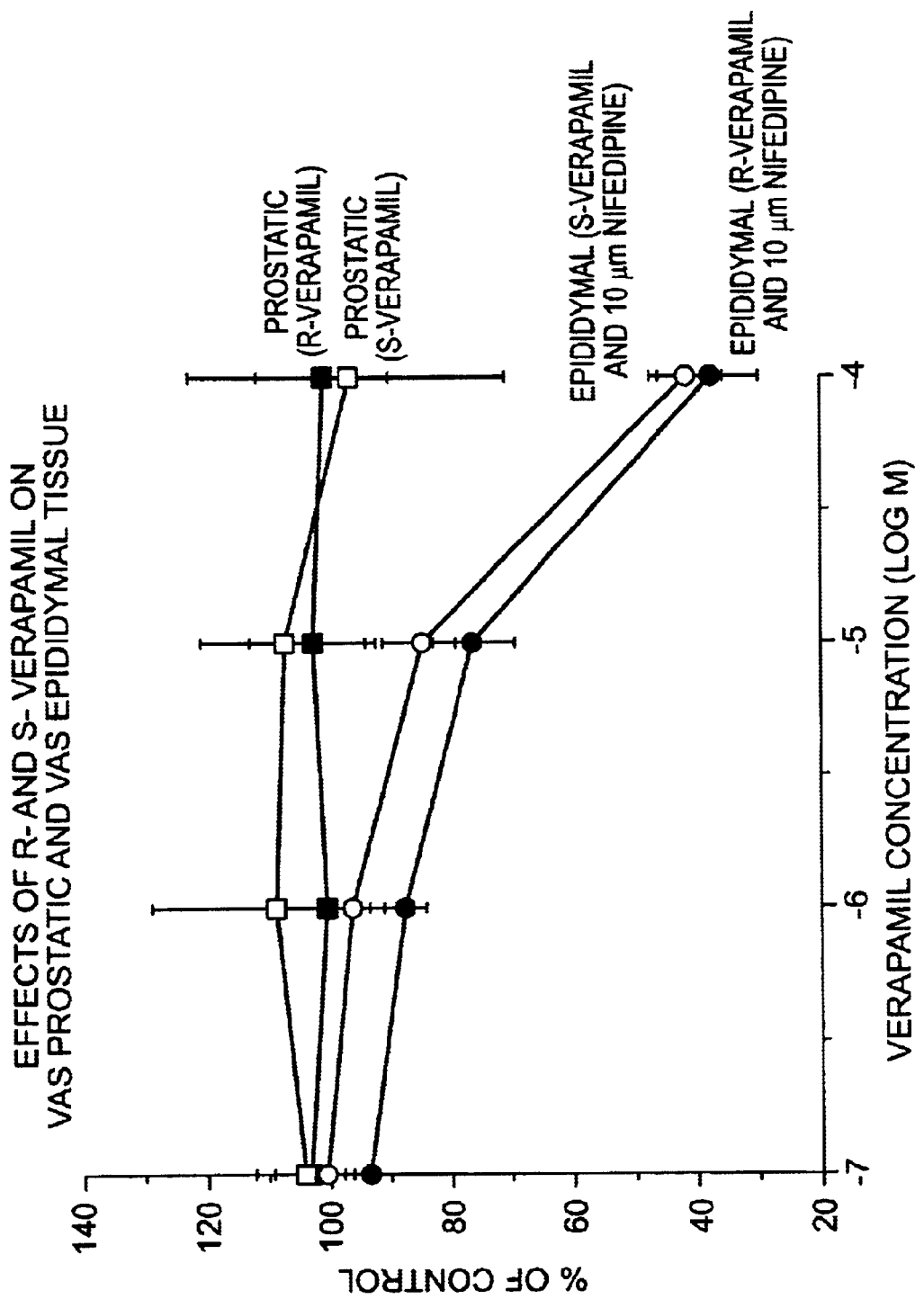

TREATMENT OF ABNORMAL INCREASES IN GASTROINTESTINAL MOTILITY WITH (R)-VERAPAMIL

This application is a continuation-in-part of U.S. application Ser. No. 10/256,261, filed Sep. 27, 2002 abandoned, the entire disclosure of which is incorporated herein by reference.

The present invention is generally directed to methods of treating, preventing, and/or managing abnormal increases in gastrointestinal motility. Such abnormal increases may be caused by one or more intestinal conditions, including, but not limited to, irritable bowel syndrome (IBS), infectious diseases of the small and large intestine, and symptoms of any of the foregoing. In particular, the invention relates to methods of treating, preventing, and/or managing abnormal increases in gastrointestinal motility with stereo-specific forms of calcium channel blockers, including but not limited to, (R)-verapamil.

Irritable Bowel Syndrome (IBS) results in about 3.5 million physician visits per year, and is the most common diagnosis made by gastroenterologists, accounting for about 25% of all patients diagnosed (Camilleri and Choi, *Aliment Pharmacol. Ther.*, 11 (1):3–15, 1997). Individuals afflicted with IBS visit doctors more frequently, enjoy a lower quality of life, and miss work more often relative to those with no bowel symptoms (Drossman et al., *Dig. Dis. Sci.*, 38:1569–1580, 1993). As a consequence, individuals suffering from IBS incur significantly higher health care costs than those without the condition (Talley et al., *Gastroenterology*, 109:1736–1741, 1995).

IBS is characterized by abdominal pain and altered bowel function (Mayer et al., *Gastroenterology*, 107:271–93, 1994; Camilleri and Choi, 1997; Drossman et al., *Am. J. Gastroent.*, 91:2270–81, 1996). The condition leads to crampy pain, gassiness, bloating, and changes in bowel habits. Some people with IBS have constipation (difficult or infrequent bowel movements); others have diarrhea (frequent loose stools, often with an urgent need to move the bowels); and some people experience both. Sometimes a person with IBS has a crampy urge to move their bowels but cannot do so. See, e.g., NIH Publication No. 97–693, National Digestive Diseases Information Clearinghouse, National Institute of Health, 1992 (also available on-line at "www.niddk.nih.gov/health/digest/pubs/irrbowel/irrbowel.htm" posted February 1998, last updated November 2000).

Through the years, IBS has been called by many names—colitis, mucous colitis, spastic colon, spastic bowel, and functional bowel disease. Most of these terms are inaccurate. Id. Colitis, for instance, means inflammation of the large intestine (colon). IBS, however, does not cause inflammation and should not be confused with inflammatory bowel diseases, such as ulcerative colitis and Crohn's disease. Id.

IBS is a well-recognized clinical entity, but no causative etiologic agents or structural or biochemical defects have been positively identified. In many patients, intraluminal contents exhibit unusually rapid transit through the length of the small intestine and colon. Afflicted patients generally complain of abdominal discomfort and report audible bowel noises, cramping and abdominal pain, an urgency to defecate, and the passage of loose stools often covered with mucus.

Due to the lack of readily identifiable structural or biochemical abnormalities associated with IBS, the medical community has developed a consensus definition and a set of criteria known as the Manning or Rome Criteria, to aid in the diagnosis of IBS (Manning et al., *Br. Med. J.*, 2:653–4, 1978; Thompson et al., *Gastroent. Int.*, 2:92–5, 1989). According to the Rome criteria, IBS is identified by abdominal pain or discomfort which is relieved by defecation and/or associated with a change in frequency or consistency of stools, plus two or more of the following: altered stool frequency, altered stool form, altered stool passage, passage of mucus, and bloating or feeling of abdominal distention (Dalton and Drossman, *Am. Fam. Physician*, 55(3):875–880, 1997).

Despite increasing diagnosis, no effective treatments have been identified for intestinal conditions such as IBS. Thus, there exists a strong need in the art for new or more effective methods for treating, preventing, and/or managing intestinal conditions such as IBS.

Verapamil (benzeneacetonitrile α-[3-[[2-(3,4-dimethoxyphenyl)ethyl]methylamino]propyl]-3,4-dimethoxy-α-(1-methylethyl) hydrochloride) is a commercially available drug that, when used to treat cardiovascular conditions, acts as a calcium ion influx inhibitor by blocking calcium ion channels. The drug is typically prescribed as a treatment for cardiovascular conditions, such as hypertension, atrial fibrillation, angina, and paroxysmal supraventricular tachycardia. The drug is normally prescribed as a racemic mixture containing approximately equal amounts of (R)-verapamil and (S)-verapamil.

The pharmacodynamics and pharmacokinetics of the (R)- and (S) stereoisomers differ. For example, the (S)-isomer is typically 10 times more potent than the (R)-isomer at treating cardiovascular conditions. In addition, stereoselective first pass liver metabolism occurs, resulting in higher systemic concentrations (i.e., bioavailability) of the (R)-isomer following oral administration of the racemate. In addition, the inhibitory potency of the isomers against sites on the calcium channel and alpha-1-adrenergic receptors is different (Piascik, *Can. J. Physiol. Pharmacol.*, 68(3): 439–446, 1990).

Verapamil causes several undesirable dose-limiting side effects. These include, inter alia, depression in myocardial activity (Satoh et al., *J. Cardio. Pharm.*, 2:309–318, 1980) and constipation (Hedner et al., *Acta Pharmacol. Toxicol.*, 58(Suppl 2):119–30, 1986; Krevsky et al., *Dig. Dis. Sci.*, 37(6):919–924, 1992; Thulin, et al., *Scand. J. Prim. Health Care Suppl.*, 1:81–84, 1990). Researchers have attempted to overcome these unwanted side effects by using the individual stereoisomers of verapamil. Harding et al. (U.S. Pat. No. 5,889,060) describe the use of a single stereoisomer, (R)-verapamil, as a treatment for angina. Others suggest that (S)-verapamil is more beneficial for treating angina and atrial fibrillation, while (R)-verapamil is useful for reversing multi-drug resistance in cancer chemotherapy (e.g., McCague et al., U.S. Pat. No. 5,910,601; Harding et al., U.S. Pat. No. 5,932,246).

Longstreth et al. (U.S. Pat. No. 5,955,500) report that the ratio of (R)- and (S)-verapamil may be manipulated to achieve desirable cardiovascular effects while minimizing adverse effects such as slowing of cardiac conduction, alteration in heart rate, and constipation. Such a strategy has led to the development of a dosage form that releases the stereoisomers of verapamil at different rates in the body for the treatment of cardiovascular conditions (Gilbert et al., U.S. Pat. 6,267,980).

Harding et al. (U.S. Pat. No. 5,932,246) report that the separate administration of either (R)- or (S)-verapamil reduces the significant constipative effects caused by racemic verapamil. The patentees suggest that this therapeutic approach may achieve the desirable cardiovascular effects of verapamil while reducing the constipation experienced by a patient undergoing treatment.

In contrast, other researchers have attempted to use the constipative effects of racemic verapamil as means for treating intestinal conditions (see, e.g., McCleod, *Med. J. Aust.*, 2(3):119 (letter), 1983). Byrne (*J. Clin. Psy.*, 48:9, 1987) describes the treatment of 3 patients diagnosed with irritable bowel syndrome, and reports that 80 mg of racemic verapamil had a constipating effect on the patients. Similarly, Ahlman et al. (*Br. J. Cancer*, 54:251–256, 1986) describe the treatment of a patient suffering from midgut carcinoid syndrome (experiencing severe bouts of diarrhea). According to Ahlman, low doses of racemic verapamil relieved the diarrhea.

Despite the reported clinical utility of racemic verapamil in treating some intestinal conditions, using the drug in this manner is dangerous because it still exerts its primary effect on the cardiovascular system. Thus, a patient being treated with racemic verapamil for intestinal conditions will likely experience significant unwanted cardiovascular effects from the use of the drug. In addition, while the above-cited reports and others have described racemic verapamil's use in treating some intestinal conditions, none of these reports has sought to identify, characterize, or use a single stereo-isomer of verapamil to treat intestinal conditions. Given the significant therapeutic drawbacks noted above, the use of racemic verapamil to treat intestinal conditions is severely limited.

Mak (U.S. Pat. No. 6,190,691) describes the use of isomers of verapamil to inhibit TNF production in cells. The reduction of TNF reportedly reduces inflammation. Thus, Mak concludes that the reduction of TNF levels will allow the use of verapamil isomers to treat certain TNF-mediated inflammatory conditions. Mak indicates that these TNF-mediated inflammatory conditions are selected from inflammatory bowel disease, rheumatoid arthritis, cachexia, asthma, Crohn's disease, endotoxin shock, adult respiratory distress syndrome, ischemic/reperfusion damage, graft-versus-host reactions, bone resorption, transplantation and lupus. Mak, however, does not describe the use of verapamil stereo-isomers to treat non-TNF mediated conditions, such as non-inflammatory conditions of the intestine.

Thus, there remains a strong need in the art for additional methods of treating, preventing, and/or managing intestinal conditions such as IBS.

The present invention is directed to new methods for treating, preventing, and/or managing abnormal increases in gastrointestinal motility using an enriched stereo-isomeric form of verapamil. The methods are based on the unexpected discovery that the (R)-isomer of verapamil exhibits a greater effect on intestinal tissue than on cardiovascular tissue. That is to say, at a given concentration, (R)-verapamil inhibits contractions in intestinal tissue to a greater extent than in cardiovascular tissue. Thus, (R)-verapamil exhibits a relative intestinal selectivity. In contrast, the more biologically potent (S)-isomer is approximately equally active in both intestinal and cardiovascular tissue. Accordingly, the (R)-isomer can be used to treat, prevent, and/or manage abnormal increases in gastrointestinal motility, while reducing or exhibiting fewer undesirable cardiovascular effects associated with the administration of (S)-verapamil or racemic mixtures of verapamil. Thus, the present invention overcomes the deficiencies and problems in the prior art and provides new and effective treatments for abnormal increases in gastrointestinal motility, and intestinal conditions that cause the same.

The methods of the invention involve administering a pharmaceutically effective amount of (R)-verapamil, or a pharmaceutically acceptable salt thereof, in enriched form, to a subject in need of such treatment, prevention, and/or management. In one embodiment, the abnormal increases in gastrointestinal motility are due to an increased frequency and/or intensity of intestinal contractions. The present invention may be used to reduce the frequency and/or intensity of such intestinal contractions, thereby slowing intestinal motility. The abnormal increases in gastrointestinal motility may be caused by one or more intestinal conditions. Thus, the present invention may be used to treat, prevent, and/or manage such intestinal condition(s). Examples of intestinal conditions that may be treated, prevented, and/or managed according to the present invention include, but are not limited to, irritable bowel syndrome (IBS), infectious diseases of the small and large intestine, and symptoms of any of the foregoing. Non-inflammatory conditions, such as IBS, are particularly amenable to the effects of the methods of the present invention. However, those of ordinary skill in the art are familiar with other types of functional intestinal conditions that produce abnormal increases in gastrointestinal motility, which may also benefit from the present invention.

FIG. 3 illustrates the effects of (R)-verapamil and (S)-verapamil on KCl-induced contractions in the rat vas prostatic and rat vas epididymal tissue.

Figure 1:
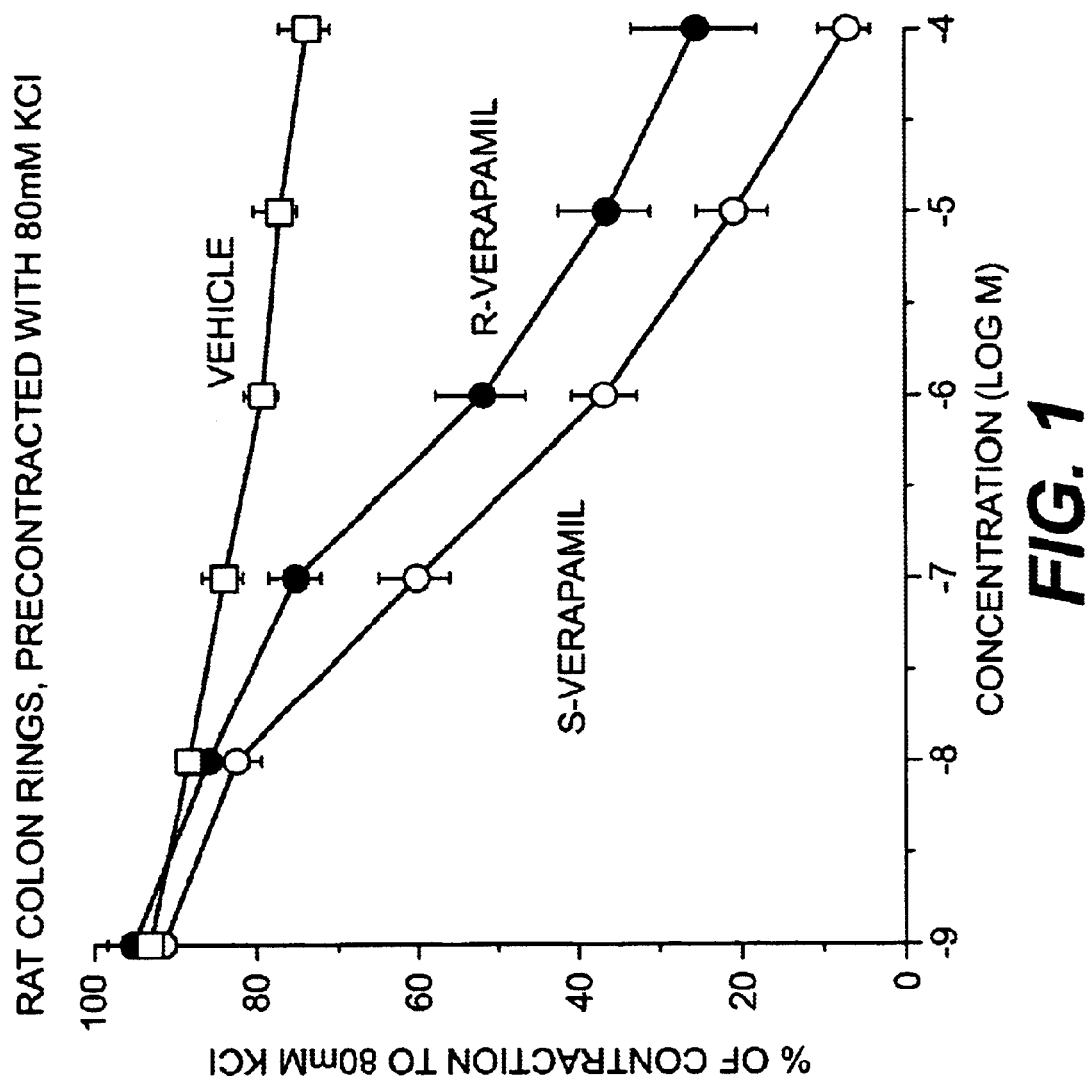
FIG. 1 illustrates the relaxation achieved by (R)-verapamil and (S)-verapamil on KCl-induced contractions in rat colon tissue.

As used herein, the phrase "modified-release" formulation or dosage form includes a pharmaceutical preparation that achieves a desired release of the drug from the formulation. For example, a modified-release formulation may extend the influence or effect of a therapeutically effective dose of an active compound in a patient. Such formulations are referred to herein as "extended-release formulations." In addition to maintaining therapeutic levels of the active compound, a modified-release formulation may also be designed to delay the release of the active compound for a specified period. Such compounds are referred to herein as "delayed onset" formulations or dosage forms. Still further, modified-release formulations may exhibit properties of both delayed and extended release formulations, and thus be referred to as "delayed-onset, extended-release" formulations.

As used herein, the term "pharmaceutically acceptable excipient" includes compounds that are compatible with the other ingredients in a pharmaceutical formulation and not injurious to the subject when administered in therapeutically effective amounts.

As used herein, the term "pharmaceutically acceptable salt" includes salts that are physiologically tolerated by a subject. Such salts are typically prepared from an inorganic and/or organic acid. Examples of suitable inorganic acids include, but are not limited to, hydrochloric, hydrobromic, hydroiodic, nitric, sulfuric, and phosphoric acid. Organic acids may be aliphatic, aromatic, carboxylic, and/or sulfonic acids. Suitable organic acids include, but are not limited to, formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

The term "racemic" as used herein means a mixture of the (R)- and (S)-enantiomers, or stereoisomers, of verapamil in which neither enantiomer, or stereoisomer, is substantially purified from the other.

The term "enriched," as used herein to describe (R)-verapamil, refer to a composition having a greater amount of (R)-verapamil than (S)-verapamil. For example, the composition may contain greater than 50%, 55%, or at least about 60% of the (R)-verapamil stereoisomer by weight, based on the total weight of verapamil. In one embodiment, the amount of enriched verapamil may be higher, for example, at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%, or any fraction thereof (i.e., 90.1%, 90.2%, etc.), of (R)-verapamil by weight, based on the total weight of verapamil. In a particular embodiment, the amount of enriched (R)-verapamil may be greater than 99%, 99.1%, 99.2%, 99.3%, 99.4%, 99.5%, 99.6%, 99.7%, 99.8%, 99.9% or may be 100%, by weight, based on the total weight of verapamil. These terms also define the amount of any pharmaceutically acceptable salts of (R)-verapamil.

The phrase "therapeutically effective amount of (R)-verapamil," as used herein, refers to the amount of enriched (R)-verapamil (or pharmaceutically acceptable salt thereof), which alone or in combination with other drugs, provides any therapeutic benefit in the prevention, treatment, and/or management of abnormal increases in gastrointestinal motility. Such abnormal increases may be caused by one or more intestinal conditions, such as irritable bowel syndrome (IBS) and infectious diseases of the small and large intestines. Thus, the enriched (R)-verapamil may provide a therapeutic benefit in the prevention, treatment, and/or management of such conditions. In one embodiment, the therapeutic amount is sufficient to achieve a therapeutic benefit while reducing and/or avoiding at least one unwanted effect (e.g., unacceptably high levels of cardiovascular activity) typically associated with administration of (S)-verapamil or racemic verapamil. In another embodiment, the therapeutic amount is sufficient to reduce the frequency and/or intensity of intestinal contractions, thereby slowing intestinal motility.

The present invention is directed to the use of enriched (R)-verapamil, or a pharmaceutically acceptable salt thereof, for preventing, treating, and/or managing abnormal increases in gastrointestinal motility. Such abnormal increases may be the result of one or more intestinal conditions including, but not limited to, irritable bowel syndrome (IBS), infectious diseases of the small or large intestine, and symptoms thereof. Such conditions may be characterized by complaints of too frequent bowel movements, usually including symptoms of diarrhea. Other conditions involving abnormally rapid gastrointestinal motility, abnormal number of bowel movements, and diarrhea, may also be treated, prevented, and/or managed using the presently disclosed methods.

Enriched (R)-verapamil may be obtained from a racemic mixture of verapamil, for example, as described in U.S. Pat. Nos. 5,892,093 and 5,910,601, the relevant disclosure of each of which is incorporated herein by reference for this purpose. Enriched (R)-verapamil may also be obtained from racemic mixtures by HPLC separation or resolution of the enantiomers using any available means, such as an optically active resolving acid. In addition, (R)-verapamil may be synthesized by stereospecific synthesis using any appropriate methodology, examples of which are well known to those of ordinary skill in the art. Stereospecific synthesis can result in products of high enantiomeric purity. In some cases in which the enantiomeric purity of the product is not sufficiently high, synthesis methods may be combined with additional separation techniques to further enhance the enantiomeric purity of the (R)-verapamil obtained. Examples of processes for resolving racemic verapamil to obtain enriched (R)-verapamil are well known to those of ordinary skill in the art.

The invention also includes pharmaceutical compositions for use in preventing, treating, and/or managing abnormal increases in gastrointestinal motility, and/or the intestinal conditions which cause the same, comprising a therapeutically effective amount of enriched (R)-verapamil, or a pharmaceutically acceptable salt thereof.

In one embodiment, the enriched (R)-verapamil, or a pharmaceutically acceptable salt thereof, is provided in a pharmaceutical composition for use in treating, preventing, and/or managing abnormal increases in gastrointestinal motility and/or the intestinal conditions which cause the same. Such compositions optionally comprise one or more pharmaceutically acceptable excipients. Suitable excipients are known to those of skill in the art and described, for example, in the Handbook of Pharmaceutical Excipients (Kibbe (ed.), $3^{rd}$ Edition (2000), American Pharmaceutical Association, Washington, D.C.), and Remington's Pharmaceutical Sciences (Gennaro (ed.), $20^{th}$ edition (2000), Mack Publishing, Inc., Easton, Pa.), which, for their disclosures relating to excipients and dosage forms, are incorporated herein by reference. For example, suitable excipients include, but are not limited to, starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, plasticizers, gelling agents, thickeners, hardeners, setting agents, suspending agents, surfactants, humectants, carriers, stabilizers, antioxidants, and combinations thereof.

The pharmaceutical compositions of the invention are typically provided in dosage forms that are suitable for administration to a subject by a desired route. A number of suitable dosage forms are described below, but are not meant to include all possible choices. One of skill in the art is familiar with the various dosage forms that are suitable for use in the present invention, as described, for example, in Remington's Pharmaceutical Sciences, which has been incorporated by reference above. The most suitable route in any given case will depend on the nature and severity of the gastrointestinal motility and/or intestinal condition being prevented, treated, and/or managed. For example, the pharmaceutical compositions may be formulated for administration orally, nasally, rectally, intravaginally, parenterally, intracisternally, and topically (including buccally and sublingually).

Formulations suitable for oral administration include, but are not limited to, capsules, cachets, pills, tablets, lozenges (using a flavored basis, usually sucrose and acacia or tragacanth), powders, granules, solutions, suspensions in an aqueous or non-aqueous liquid, oil-in-water or water-in-oil liquid emulsions, elixirs, syrups, pastilles (using an inert base, such as gelatin and glycerin, or sucrose and acacia), mouth washes, pastes, and the like; each containing a predetermined amount of (R)-verapamil to provide a therapeutic amount of the drug in one or more doses.

In solid dosage forms for oral administration (capsules, tablets, pills, powders, granules and the like), the (R)-verapamil is typically mixed with one or more pharmaceutically-acceptable excipients, including carriers, such as sodium citrate or dicalcium phosphate; fillers or extenders, such as starches, spray-dried or anhydrous lactose, sucrose, glucose, mannitol, dextrose, sorbitol, cellulose (e.g., microcrystalline cellulose; AVICEL™), dihydrated or anhydrous dibasic calcium phosphate, and/or silicic acid; binders, such as acacia, alginic acid, carboxymethylcellulose (sodium), cellulose (microcrystalline), dextrin, ethylcellulose, gelatin, glucose (liquid), guar gum, hydroxypropyl cellulose, hydroxypropyl methylcellulose, methylcellulose (e.g., methylcellulose 2910), polyethylene oxide, povidone, starch (pregelatinized) or syrup; humectants, such as glycerol; disintegrating agents, such as agar, calcium carbonate, potato or tapioca starch, alginic acid, certain silicates, pregelatinized starch, sodium starch glycolate (EXPLOTAB™), crosslinked providone, crosslinked sodium carboxymethylcellulose, clays, microcrystalline cellulose (e.g., AVICEL™), alginates, gums, and/or sodium carbonate; solution retarding agents, such as paraffin; absorption accelerators, such as quaternary ammonium compounds; wetting agents, such as cetyl alcohol or glycerol monostearate; absorbents, such as kaolin and bentonite clay; lubricants, such as talc, calcium stearate, magnesium stearate, solid polyethylene glycols, steric acid, sodium stearyl fumarate, magnesium lauryl sulfate, hydrogenated vegetable oil, and/or sodium lauryl sulfate; glidants, such as calcium silicate, magnesium silicate, colloidal anahydrous silica, and/or talc; flavoring agents, such as synthetic flavor oils and flavoring aromatics, natural oils, extracts from plant leaves, flowers, and fruits, including cinnamon oil, oil of wintergreen, peppermint oils, bay oil, anise oil, eucalyptus, thyme oil, vanilla, citrus oil (e.g., lemon, orange, grape, lime, and grapefruit), fruit essences (e.g., apple, banana, pear, peach, strawberry, raspberry, cherry, plum, pineapple, apricot, as so forth); coloring agents and/or pigments, such as titanium dioxide and/or dyes approved for use in food and pharmaceuticals; buffering agents; dispersing agents; preservatives; and/or diluents. The aforementioned excipients are given as examples only and are not meant to include all possible choices.

Any of these solid dosage forms may optionally be scored or prepared with coatings and shells, such as enteric coatings, and coatings for modifying the rate of release, examples of which are well known in the pharmaceutical-formulating art. For example, such coatings may comprise sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methyl cellulose phthalate, methacrylic acid copolymer, methylcellulose, polyethylene glycol, polyvinyl acetate phthalate, shellac, sucrose, titanium dioxide, wax, or zein. In one embodiment, the coating material comprises hydroxypropyl methylcellulose. The coating material may further comprise antiadhesives, such as talc; plasticizers (depending on the type of coating material selected), such as castor oil, diacetylated monoglycerides, dibutyl sebacate, diethyl phthalate, glycerin, polyethylene glycol, propylene glycol, triacetin, triethyl citrate; opacifiers, such as titanium dioxide; and/or coloring agents and/or pigments. The coating process may be carried out by any suitable means, for example, by using a perforated pan system such as the GLATT™, ACCELACOTA™, and/or HICOATER™ apparatuses.

Tablets may be formed by any suitable process, which are known to those of ordinary skill in the art. For example, the ingredients may be dry-granulated or wet-granulated by mixing in a suitable apparatus before tabletting. Granules of the ingredients to be tabletted may also be prepared using suitable spray/fluidization or extrusion/spheronsation techniques.

With quick-release tablets, the choice of excipients generally allows a fast dissolution. The tablets may be conventional instant release tablets designed to be taken whole in the typical administration manner (i.e., with sufficient amount of water to facilitate swallowing). Alternatively the tablets may be formulated with suitable excipients to act as a fast dissolving and/or fast melting tablet in the oral cavity. Also, the tablet can be in the form of a chewable or effervescent dosage form. With effervescent dosage forms, the tablet is typically added to a suitable liquid that causes it to disintegrate, dissolve, and/or disperse.

Tablets typically are designed to have an appropriate hardness and friability to facilitate manufacture on an industrial scale using equipment to produce tablets at high speed. Also the tablets are usually packed or filled in all kinds of containers. If the tablet has an insufficient hardness or is friable, the tablet that is taken by the subject may be broken or crumbled into powder. As a consequence of this insufficient hardness or friability, the subject can no longer be certain that the amount of the dose is correct. It should be noted that the hardness of tablets, amongst other properties, is influenced by the shape of the tablets. Different shapes of tablets may be used according to the present invention. Tablets may be circular, oblate, oblong, or any other shape that is known in the art. The shape of the tablets may also influence the disintegration rate.

Any of the solid compositions may encapsulated in soft and hard gelatin capsules using any of the excipients described above. For example, the encapsulated dosage form may include fillers, such as lactose and microcrystalline; glidants, such as colloidal silicon dioxide and talc; lubricants, such as magnesium stearate; and disintegrating agents, such as starch (e.g., maize starch). Using capsule filling equipment, the ingredients to be encapsulated are milled together, sieved, mixed, packed together, and then delivered into a capsule. The lubricants may be present in an amount from about 0.5% (w/w) to about 2.0% (w/w). In one embodiment, the lubricant is about 1.25% (w/w) of the content of the capsule.

The (R)-verapamil may also be formulated into a liquid dosage form for oral administration. Suitable formulations include emulsions, microemulsions, solutions, suspensions, syrups and elixirs. These formulations optionally include diluents commonly used in the art, such as, for example, water or other solvents, solubilizing agents and emulsifiers, including, but not limited to, ethyl alcohol, isopropyl alcohol, ethyl carbonate, ethyl acetate, benzyl alcohol, benzyl benzoate, propylene glycol, 1,3-butylene glycol, oils, glycerol, tetrahydrofuryl alcohol, polyethylene glycols, fatty acid esters of sorbitan, and mixtures thereof. In addition, the liquid formulations optionally include adjuvants such as wetting agents, emulsifying and suspending agents, sweetening, flavoring, coloring, perfuming and preservative agents. Suitable suspension agents include, but are not limited to, ethoxylated isostearyl alcohols, polyoxyethylene sorbitol and sorbitan esters, microcrystalline cellulose, aluminum metahydroxide, bentonite, agar-agar and tragacanth, xanthan gum, hydroxypropylmethylcellulose, methylcellulose, carageenan, sodium carboxymethyl cellulose, and sodium carboxymethyl cellulose/microcrystalline cellulose mixtures, sodium carboxymethyl cellulose/microcrystalline cellulose mixtures, and/or mixtures thereof. In one embodiment, the suspending agent comprises xanthan gum, carageenan, sodium carboxymethyl cellulose/microcrystalline cellulose mixtures, and/or mixtures thereof. In another embodiment, the suspending agent is AVICEL™ RC591, AVICEL™ RC581, and/or AVICEL™

CL611 (Avicel is a trademark of FMC Corporation); and/or RC591, RC581 and CL611 (mixtures of microcrystalline cellulose and sodium carboxymethyl cellulose).

The amount of suspending agent present will vary according to the particular suspending agent used and the presence or absence of other ingredients which have an ability to act as a suspending agent or contribute significantly to the viscosity of the composition. The suspension may also contain ingredients which improve its taste, for example sweeteners; bitter-taste maskers, such as sodium chloride; taste-masking flavours, such as contramarum; flavour enhancers, such as monosodium glutamate; and flavouring agents. Examples of sweeteners include bulk sweeteners, such as sucrose, hydrogenated glucose syrup, the sugar alcohols sorbitol and xylitol; and sweetening agents such as sodium cyclamate, sodium saccharin, aspartame, and ammonium glycyrrhizinate. The liquid formulations may further comprise one or more buffering agents, as needed, to maintain the desired pH.

The liquid formulations of the present invention may also be filled into soft gelatin capsules. For example, the liquid may include a solution, suspension, emulsion, microemulsion, precipitate, or any other desired liquid media carrying the (R)-verapamil. The liquid may be designed to improve the solubility of the (R)-verapamil upon release, or may be designed to form a drug-containing emulsion or dispersed phase upon release. Examples of such techniques are well known in the art. Soft gelatin capsules may be coated, as desired, with a functional coating, as described below, to delay the release of the drug.

For rectal or vaginal administration, the composition may be provided as a suppository. Suppositories optionally comprise one or more non-irritating excipients, for example, polyethylene glycol, a suppository wax, or a salicylate. Such excipients may be selected on the basis of desirable physical properties. For example, a compound that is solid at room temperature but liquid at body temperature will melt in the rectum or vaginal cavity and release the active compound. The formulation may alternatively be provided as an enema for rectal delivery. Formulations suitable for vaginal administration also include pessaries, tampons, creams, gels, pastes, foams or spray formulations containing such carriers, examples of which are known in the art.

Formulations suitable for topical or transdermal administration include powders, sprays, ointments, pastes, creams, lotions, gels, solutions, patches and inhalants. Such formulations optionally contain excipients such as animal and vegetable fats, oils, waxes, paraffins, starch, tragacanth, cellulose derivatives, polyethylene glycols, silicones, bentonites, silicic acid, talc, zinc oxide, or mixtures thereof. Powders and sprays may also contain excipients such as lactose, talc, silicic acid, aluminum hydroxide, calcium silicates and polyamide powder. Additionally, sprays may contain propellants, such as chlorofluoro-hydrocarbons and volatile unsubstituted hydrocarbons, such as butane and propane.

Transdermal patches have the added advantage of providing controlled delivery of the mixture of the invention to the body. Such dosage forms can be made by dissolving, dispersing or otherwise incorporating a pharmaceutical composition containing (R)-verapamil in a suitable medium, such as an elastomeric matrix material. Absorption enhancers can also be used to increase the flux of the mixture across the skin. The rate of such flux can be controlled by either providing a rate-controlling membrane or dispersing the compound in a polymer matrix or gel.

For parenteral administration, such as administration by injection (including, but not limited to, subcutaneous, bolus injection, intramuscular, intraperitoneal, and intravenous), the pharmaceutical compositions may be formulated as isotonic suspensions, solutions or emulsions in oily or aqueous vehicles, and may contain formulatory agents such as suspending, stabilizing, or dispersing agents. Alternatively, the compositions may be provided in dry form such as a powder, crystalline or freeze-dried solid for reconstitution with sterile pyrogen-free water or isotonic saline before use. They may be presented, for example, in sterile ampoules or vials.

Examples of suitable aqueous and nonaqueous excipients include water, ethanol, polyols (such as glycerol, propylene glycol, polyethylene glycol, and the like), oils, injectable organic esters, and mixtures thereof. Proper fluidity can be maintained, for example, by the use of coating materials and surfactants.

These compositions may also contain adjuvants such as preservatives, wetting agents, emulsifying agents and dispersing agents. Prevention of the action of microorganisms may be acheived by the inclusion of various antibacterial and/or antifungal agents, for example, paraben, chlorobutanol, phenol sorbic acid, and the like. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In order to prolong the therapeutic effect of a drug, it is often desirable to slow the absorption of the drug from a subcutaneous or intramuscular injection. This may be accomplished by the use of a liquid suspension of crystalline or amorphous material having low solubility. The rate of absorption of the drug then depends upon its rate of dissolution which, in turn, may depend upon crystal size and crystalline form. Alternatively, delayed absorption of a parenterally-administered form can be accomplished by dissolving or suspending the drug in an oil vehicle.

In addition to the common dosages forms described above, the compositions of the present invention may be formulated into a dosage form that modifies the release of (R)-verapamil. Examples of suitable modified release formulations, which may be used in accordance with the present invention include, but are not limited to, matrix systems, osmotic pumps, and membrane controlled dosage forms. These formulations typically comprise (R)-verapamil and/or one or more pharmaceutically acceptable salts thereof. Suitable pharmaceutically acceptable salts are discussed above.

Different types of modified dosage forms are briefly described below. A more detailed discussion of such forms may also be found in, for example *The Handbook of Pharmaceutical Controlled Release Technology*, D. L. Wise (ed.), Marcel Dekker, Inc., New York (2000); and also in *Treatise on Controlled Drug Delivery: Fundamentals, Optimization, and Applications*, A. Kydonieus (ed.), Marcel Dekker, Inc., New York, (1992), the relevant contents of each of which is hereby incorporated by reference for this purpose. Examples of modified release dosage forms are also described, for example, in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which, for their discussions of pharmaceutical formulations, are incorporated herein by reference.

Advantages of modified-release formulations may include extended activity of the drug, reduced dosage frequency, increased patient compliance, and the ability to deliver the drug to specific sites in the intestinal tract. Suitable components (e.g., polymers, excipients, etc.) for use in modified-release formulations, and methods of producing the same, are also described, e.g., in U.S. Pat. No. 4,863,742, which is incorporated by reference for these purposes.

Matrix-Based Dosage Forms

In some embodiments, the modified release formulations of the present invention are provided as matrix-based dosage forms. Matrix formulations according to the invention may include hydrophilic, e.g., water-soluble, and/or hydrophobic, e.g., water-insoluble, polymers. The matrix formulations of the present invention may optionally be prepared with functional coatings, which may be enteric, e.g., exhibiting a pH-dependent solubility, or non-enteric, e.g., exhibiting a pH-independent solubility.

Matrix formulations of the present invention may be prepared by using, for example, direct compression or wet granulation. A functional coating, as noted above, may then be applied in accordance with the invention. Additionally, a barrier or sealant coat may be applied over a matrix tablet core prior to application of a functional coating. The barrier or sealant coat may serve the purpose of separating an active ingredient from a functional coating, which may interact with the active ingredient, or it may prevent moisture from contacting the active ingredient. Details of barriers and sealants are provided below.

In a matrix-based dosage form in accordance with the present invention, the (R)-verapamil and optional pharmaceutically acceptable excipient(s) are dispersed within a polymeric matrix, which typically comprises one or more water-soluble polymers and/or one or more water-insoluble polymers. The drug may be released from the dosage form by diffusion and/or erosion. Such matrix systems are described in detail by Wise and Kydonieus, supra.

Suitable water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Suitable water-insoluble polymers include, but are not limited to, ethylcellulose, cellulose acetate cellulose propionate, cellulose acetate propionate, cellulose acetate butyrate, cellulose acetate phthalate, cellulose triacetate, poly(methyl methacrylate), poly(ethyl methacrylate), poly (butyl methacrylate), poly(isobutyl methacrylate), and poly (hexyl methacrylate), poly(isodecyl methacrylate), poly (lauryl methacrylate), poly(phenyl methacrylate), poly (methyl acrylate), poly(isopropyl acrylate), poly(isobutyl acrylate), poly(octadecyl acrylate), poly(ethylene), poly (ethylene) low density, poly(ethylene) high density, poly (ethylene oxide), poly(ethylene terephthalate), poly(vinyl isobutyl ether), poly(vinyl acetate), poly(vinyl chloride) or polyurethane, and/or mixtures thereof.

Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl cellulose, alginates, gelatin, polyvinyl pyrrolidone, sucrose and acacia; humectants, such as glycerol; disintegrating agents, such as agar, calcium carbonate, potato and tapioca starch, alginic acid, certain silicates, EXPLOTAB™, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients may have more than one role or function, or be classified in more than one group; the classifications are descriptive only, and not intended to limit any use of a particular excipient.

In one embodiment, a matrix-based dosage form comprises (R)-verapamil; a filler, such as starch, lactose, or microcrystalline cellulose (AVICEL™); a binder/controlled-release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulfate or polysorbates; and a glidant, such as colloidal silicon dioxide (AEROSIL™) or talc.

The amounts and types of polymers, and the ratio of water-soluble polymers to water-insoluble polymers in the inventive formulations are generally selected to achieve a desired release profile of (R)-verapamil. For example, by increasing the amount of water-insoluble-polymer relative to the amount of water-soluble polymer, the release of the drug may be delayed or slowed. This is due, in part, to an increased impermeability of the polymeric matrix, and, in some cases, to a decreased rate of erosion during transit through the GI tract.

Osmotic Pump Dosage Forms

In another embodiment, the modified release formulations of the present invention are provided as osmotic pump dosage forms. In an osmotic pump dosage form, a core containing the (R)-verapamil and optionally one or more osmotic excipients is typically encased by a selectively permeable membrane having at least one pore or orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the pores or orifice(s) in an attempt to equalize the osmotic pressure across the selectively permeable membrane.

In more complex pumps, the dosage form may contain two internal compartments in the core. The first compartment contains the drug and the second compartment may contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. The osmotic pumps useful in accordance with the present invention may be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

One or more delivery orifices may be drilled through the selectively permeable membrane wall. Alternatively, one or more orifices in the wall may be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), cellulose acetate, cellulose diacetate, cellulose triacetate, and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

As discussed above, the osmotic pump dosage form may contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as into increase the hydrostatic pressure within the dosage form. The polymers may swell or expand to a very high degree, usually exhibiting a 2- to 50-fold volume increase. The polymers can be non-cross-linked or cross-linked. In one embodiment, the swellable polymers are hydrophilic polymers. Suitable polymers include, but are not limited to, poly(hydroxy alkyl methacrylate) having a molecular weight of from 30,000 to 5,000,000; kappa-carrageenan; polyvinylpyrrolidone having a molecular weight of from 10,000 to 360,000; anionic and cationic hydrogels; polyelectrolyte complexes; poly(vinyl alcohol) having low amounts of acetate, cross-linked with glyoxal, formaldehyde, or glutaraldehyde, and having a degree of polymerization from 200 to 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene or isobutylene; water-swellable polymers of N-vinyl lactams; and/or mixtures of any of the foregoing.

The term "orifice" as used herein comprises means and methods suitable for releasing the drug from the dosage form. The expression includes one or more apertures or orifices that have been bored through the selectively permeable membrane by mechanical procedures. Alternatively, an orifice may be formed by incorporating an erodible element, such as a gelatin plug, in the selectively permeable membrane. In such cases, the pores of the selectively permeable membrane form a "passageway" for the passage of the drug. Such "passageway" formulations are described, for example, in U.S. Pat. No. Nos. 3,845,770 and 3,916,899, the relevant disclosures of which are incorporated herein by reference for this purpose.

The osmotic pumps useful in accordance with this invention may be manufactured by techniques known in the art. For example, the drug and other ingredients may be milled together and pressed into a solid having the desired dimensions (e.g., corresponding to the first compartment). The swellable polymer is then formed, placed in contact with the drug, and both are surrounded with the selectively permeable agent. If desired, the drug component and polymer component may be pressed together before applying the selectively permeable membrane. The selectively permeable membrane may be applied by any suitable method, for example, by molding, spraying, or dipping.

Membrane-Controlled Dosage Forms

The modified release formulations of the present invention may also be provided as membrane controlled formulations. Membrane controlled formulations of the present invention can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and functional coating, a barrier or sealant may be applied. Details of membrane-controlled dosage forms are provided below.

In one embodiment, the (R)-verapamil may be provided in a multiparticulate membrane controlled formulation. The (R)-verapamil may be formed into an active core by applying the drug to a nonpareil seed having an average diameter in the range of about 0.4 to about 1.1 mm or about 0.85 to about 1.00 mm. The (R)-verapamil may be applied with or without additional excipients onto the inert cores, and may be sprayed from solution or suspension using a fluidized bed coater (e.g., Wurster coating) or pan coating system. Alternatively, the (R)-verapamil may be applied as a powder onto the inert cores using a binder to bind the (R)-verapamil onto the cores. Active cores may also be formed by extrusion of the core with suitable plasticizers (described below) and any other processing aids as necessary.

The modified release formulations of the present invention comprise at least one polymeric material, which is applied as a membrane coating to the drug-containing cores. Suitable water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Suitable water-insoluble polymers include, but are not limited to, ethylcellulose, cellulose acetate cellulose propionate, cellulose acetate propionate, cellulose acetate butyrate, cellulose acetate phthalate, cellulose triacetate, poly(methyl methacrylate), poly(ethyl methacrylate), poly (butyl methacrylate), poly(isobutyl methacrylate), and poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride) or polyurethane, and/or mixtures thereof.

EUDRAGIT™ polymers (available from Rohm Pharma) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers which are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

In one embodiment comprising a membrane-controlled dosage form, the polymeric material comprises methacrylic acid co-polymers, ammonio methacrylate co-polymers, or a mixture thereof. Methacrylic acid co-polymers such as EUDRAGIT™ S and EUDRAGIT™ L (Rohm Pharma) are particularly suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material may exhibit a solubility at a pH between the pHs at which EUDRAGIT™ L and EUDRAGIT™ S are separately soluble.

The membrane coating may comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water-insoluble polymers. Alternatively, the membrane coating may comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

Ammonio methacrylate co-polymers such as Eudragit RS and Eudragit RL (Rohm Pharma) are suitable for use in the controlled release formulations of the present invention. These polymers are insoluble in pure water, dilute acids, buffer solutions, or digestive fluids over the entire physiological pH range. The polymers swell in water and digestive fluids independently of pH. In the swollen state they are then permeable to water and dissolved actives. The permeability of the polymers depends on the ratio of ethylacrylate (EA), methyl methacrylate (MMA), and trimethylammonioethyl methacrylate chloride (TAMCI) groups in the polymer. Those polymers having EA:MMA:TAMCI ratios of 1:2:0.2 (Eudragit RL) are more permeable than those with ratios of 1:2:0.1 (Eudragit RS). Polymers of Eudragit RL are insoluble polymers of high permeability. Polymers of Eudragit RS are insoluble films of low permeability.

The ammonio methacrylate co-polymers may be combined in any desired ratio. For example, a ratio of Eudragit RS:Eudragit RL (90:10) may be used. The ratios may furthermore be adjusted to provide a delay in release of the drug. For example, the ratio of Eudragit RS:Eudragit RL may be about 100:0 to about 80:20, about 100:0 to about 90:10, or any ratio in between. In such formulations, the less permeable polymer Eudragit RS would generally comprise the majority of the polymeric material.

The ammonio methacrylate co-polymers may be combined with the methacrylic acid co-polymers within the polymeric material in order to achieve the desired delay in release of the drug. Ratios of ammonio methacrylate co-polymer (e.g., Eudragit RS) to methacrylic acid co-polymer in the range of about 99:1 to about 20:80 may be used. The two types of polymers can also be combined into the same polymeric material, or provided as separate coats that are applied to the core.

In addition to the Eudragit polymers described above, a number of other such copolymers may be used to control drug release. These include methacrylate ester co-polymers (e.g., Eudragit NE 30D). Further information on the Eudragit polymers can be found in "Chemistry and Application Properties of Polymethacrylate Coating Systems," in *Aqueous Polymeric Coatings for Pharmaceutical Dosage Forms*, ed. James McGinity, Marcel Dekker Inc., New York, pg 109–114).

The coating membrane may further comprise one or more soluble excipients so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose and sucrose, sugar alcohols such as lactitol, maltitol, mannitol, sorbitol and xylitol, xanthan gum, dextrins, and maltodextrins. In some embodiments, polyvinyl pyrrolidone, mannitol, and/or polyethylene glycol can be used as soluble excipients. The soluble excipient(s) may be used in an amount of from about 1% to about 10% by weight, based on the total dry weight of the polymer.

In another embodiment, the polymeric material comprises one or more water-insoluble polymers, which are also insoluble in gastrointestinal fluids, and one or more water-soluble pore-forming compounds. For example, the water-insoluble polymer may comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds may be uniformly or randomly distributed throughout the water-insoluble polymer. Typically, the pore-forming compounds comprise about 1 part to about 35 parts for each about 1 to about 10 parts of the water-insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane may also be coated with an enteric coating, as described herein, to inhibit release in the stomach.

In one embodiment, such pore forming controlled release dosage forms comprise (R)-verapamil; a filler, such as starch, lactose, or microcrystalline cellulose (AVICEL™); a binder/controlled release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulphate or polysorbates; and a glidant, such as colloidal silicon dioxide (AEROSIL™) or talc.

The polymeric material may also include one or more auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 2% to about 300% by weight, and can range from about 20 to about 100%, based on the total dry weight of the polymer. In one embodiment, talc is the filler.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10, 20, 30, 40, or 50%, based on the weight of the dry polymer.

Anti-foaming agents can also be included. In one embodiment, the anti-foaming agent is simethicone. The amount of anti-foaming agent used typically comprises from about 0% to about 0.5% of the final formulation.

The amount of polymer to be used in the membrane controlled formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 10 to about 100% weight gain to the cores. In one embodiment, the weight gain from the polymeric material ranges from about 25 to about 70%.

The combination of all solid components of the polymeric material, including co-polymers, fillers, plasticizers, and optional excipients and processing aids, typically provides an about 10 to about 450% weight gain on the cores. In one embodiment, the weight gain is about 30 to about 160%.

The polymeric material can be applied by any known method, for example, by spraying using a fluidized bed coater (e.g., Wurster coating) or pan coating system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at any temperature above room temperature.

A sealant or barrier can also be applied to the polymeric coating. A sealant or barrier layer may also be applied to the core prior to applying the polymeric material. A sealant or barrier layer is not intended to modify the release of (R)-verapamil. Suitable sealants or barriers are permeable or soluble agents such as hydroxypropyl methylcellulose, hydroxypropyl cellulose, hydroxypropyl ethylcellulose, and xanthan gum.

Other agents can be added to improve the processability of the sealant or barrier layer. Such agents include talc, colloidal silica, polyvinyl alcohol, titanium dioxide, micronized silica, fumed silica, glycerol monostearate, magnesium trisilicate and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000 and OPADRY OY/B/28920 WHITE, each of which is available from Colorcon Limited, England.

The invention also provides an oral dosage form containing a multiparticulate (R)-verapamil formulation as hereinabove defined, in the form of caplets, capsules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal. The dosage forms can be prepared from the multiparticulates in a manner known in the art and include additional pharmaceutically acceptable excipients, as desired.

All of the particular embodiments described above, including but not limited to, matrix-based, osmotic pump-based, soft gelatin capsules, and/or membrane-controlled forms, which may further take the form of monolithic and/or multi-unit dosage forms, may have a functional coating. Such coatings generally serve the purpose of delaying the release of the drug for a predetermined period. For example, such coatings may allow the dosage form to pass through the stomach without being subjected to stomach acid or digestive juices. Thus, such coatings may dissolve or erode upon reaching a desired point in the gastrointestinal tract, such as the upper intestine.

Such functional coatings may exhibit pH-dependent or pH-independent solubility profiles. Those with pH-independent profiles generally erode or dissolve away after a predetermined period, and the period is generally directly proportional to the thickness of the coating. Those with pH-dependent profiles, on the other hand, may maintain their integrity while in the acid pH of the stomach, but quickly erode or dissolve upon entering the more basic upper intestine.

Thus, a matrix-based, osmotic pump-based, or membrane-controlled formulation may be further coated with a functional coating that delays the release of the drug. For example, a membrane-controlled formulation may be coated with an enteric coating that delays the exposure of the membrane-controlled formulation until the upper intestine is reached. Upon leaving the acidic stomach and entering the more basic intestine, the enteric coating dissolves. The membrane-controlled formulation then is exposed to gastrointestinal fluid, and then releases the (R)-verapamil over an extended period, in accordance with the invention. Examples of functional coatings such as these are well known to those in the art.

Any of the oral dosage forms described herein may be provided in the form of caplets, capsules, beads, granules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal.

The thickness of the polymer in the formulations, the amounts and types of polymers, and the ratio of water-soluble polymers to water-insoluble polymers in the modified-release formulations are generally selected to achieve a desired release profile of (R)-verapamil. For example, by increasing the amount of water-insoluble-polymer relative to the water-soluble polymer, the release of the drug may be delayed or slowed.

The amount of the dose administered, as well as the dose frequency, will vary depending on the particular dosage form used and route of administration. The amount and frequency of administration will also vary according to the age, body weight, and response of the individual subject. Typical dosing regimens can readily be determined by a competent physician without undue experimentation. It is also noted that the clinician or treating physician will know how and when to interrupt, adjust, or terminate therapy in conjunction with individual subject response.

In general, the total daily dosage for treating, preventing, and/or managing the abnormal increases in gastrointestinal motility and/or the intestinal conditions that cause the same with any of the formulations according to the present invention is from about 1 mg to about 1000 mg, or about 1, 5, 10, 15, 20, 25, 30, 35, 40, 45, 50, 55, 60, 70, 80, 90, 100, 120, 140, 150, 160, 180, 200, 250, 300, 350, 400, 450, 500, 550, 600, 650, 700, 750, 800, 850, 900, 950, or 1000 mg, or any number in between, of enriched (R)-verapamil, or a pharmaceutically acceptable salt thereof. For example, for an orally administered dosage form, the total daily dose may range from about 30 mg to about 600 mg, or from about 60 mg to about 480 mg, or from about 120 mg to about 480 mg, or from about 120 mg to about 240 mg. Accordingly, a single oral dose may be formulated to contain about 1, 5, 10, 15, 20, 25, 30, 35, 40, 45, 50, 55, 60, 70, 80, 90, 100, 120, 140, 150, 160, 180, 200, 220, 240, 250, 260, 280, 300, 320, 340, 350, 360, 380, 400, 420, 440, 450, 460, 480, 500, 520, 540, 550, 560, 580, or 600 mg, or any number in between, of enriched (R)-verapamil. The pharmaceutical compositions containing enriched (R)-verapamil may be administered in single or divided doses 1, 2, 3, 4, or more times each day. Alternatively, the dose may be delivered once every 2, 3, 4, 5, or more days. In one embodiment, the pharmaceutical compositions are administered once per day.

Any of the pharmaceutical compositions and dosage forms described herein may further comprise one or more pharmaceutically active compounds other than enriched (R)-verapamil. Such compounds may be included to treat, prevent, and/or manage the same condition being treated, prevented, and/or managed with (R)-verapamil, or a different one. Those of skill in the art are familiar with examples of the techniques for incorporating additional active ingredients into compositions comprising enriched (R)-verapamil. Alternatively, such additional pharmaceutical compounds may be provided in a separate formulation and co-administered to a subject with an enriched (R)-verapamil composition according to the present invention. Such separate formulations may be administered before, after, or simultaneously with the administration of the (R)-verapamil compositions of the present invention.

The invention is further illustrated by reference to the following examples. It will be apparent to those skilled in the art that many modifications, both to the materials and methods, may be practiced without departing from the purpose and scope of the invention.

EXAMPLES

Example 1

Activity of (R)-Verapamil and (S)-Verapamil in the Colon (S)-Verapamil and (R)-Verapamil were obtained from Aonima Materie Sintetiche E Affini S.P.A. (Milan, Italy). Rat colon tissue was prepared and mounted in a tissue bath by standard methods familiar to those skilled in the art. The physiological medium contained KCl at a concentration of 80 mM, which produces contractions of the colon tissue. The colon tissue was then treated with increasing concentrations of (R)-verapamil, (S)-verapamil, or inactive control, and the resulting reduction in tissue contractions measured. The dihydropyridine calcium antagonist nifedipine was also studied for comparison. Potency was expressed as the concentration producing 50% of KCl concentrations ($IC_{50}$) or as the negative logarithm of the $IC_{50}$ ($pIC_{50}$).

The inactive control reduced contractions in a time-dependent manner by only about 20% (FIG. 1). In contrast, both (R)- and (S)-verapamil produced more pronounced concentration-dependent relaxations. The (S)-verapamil ($IC_{50}$ of $2.95 \times 10^{-7}$) was approximately 3 times more potent than the (R)-verapamil ($IC_{50}$ of $8.51 \times 10^{-7}$) at the concentrations tested (1–100 μM). (S)-verapamil yielded a pIC50 (–log M) of $6.53 \pm 0.13$, while that for (R)-verapamil was $6.07 \pm 0.16$ (n=7 each, P<0.05). Thus, both (R)- and (S)-verapamil were active in the colon, with (S)-verapamil showing a slightly higher potency.

Example 2

Activity of (R)-Verapamil and (S)-Verapamil in the Aorta

Rat aortic tissue was prepared and mounted in a tissue bath by standard methods familiar to those skilled in the art. The physiological medium contained KCl at a concentration of 80 mM, which produces contractions of the aortic tissue. The tissue was then treated with increasing concentrations of (R)-verapamil, (S)-verapamil, or inactive control and the resulting reduction in tissue contractions measured. The dihydropyridine calcium antagonist nifedipine was also studied for comparison.

Figure 2:
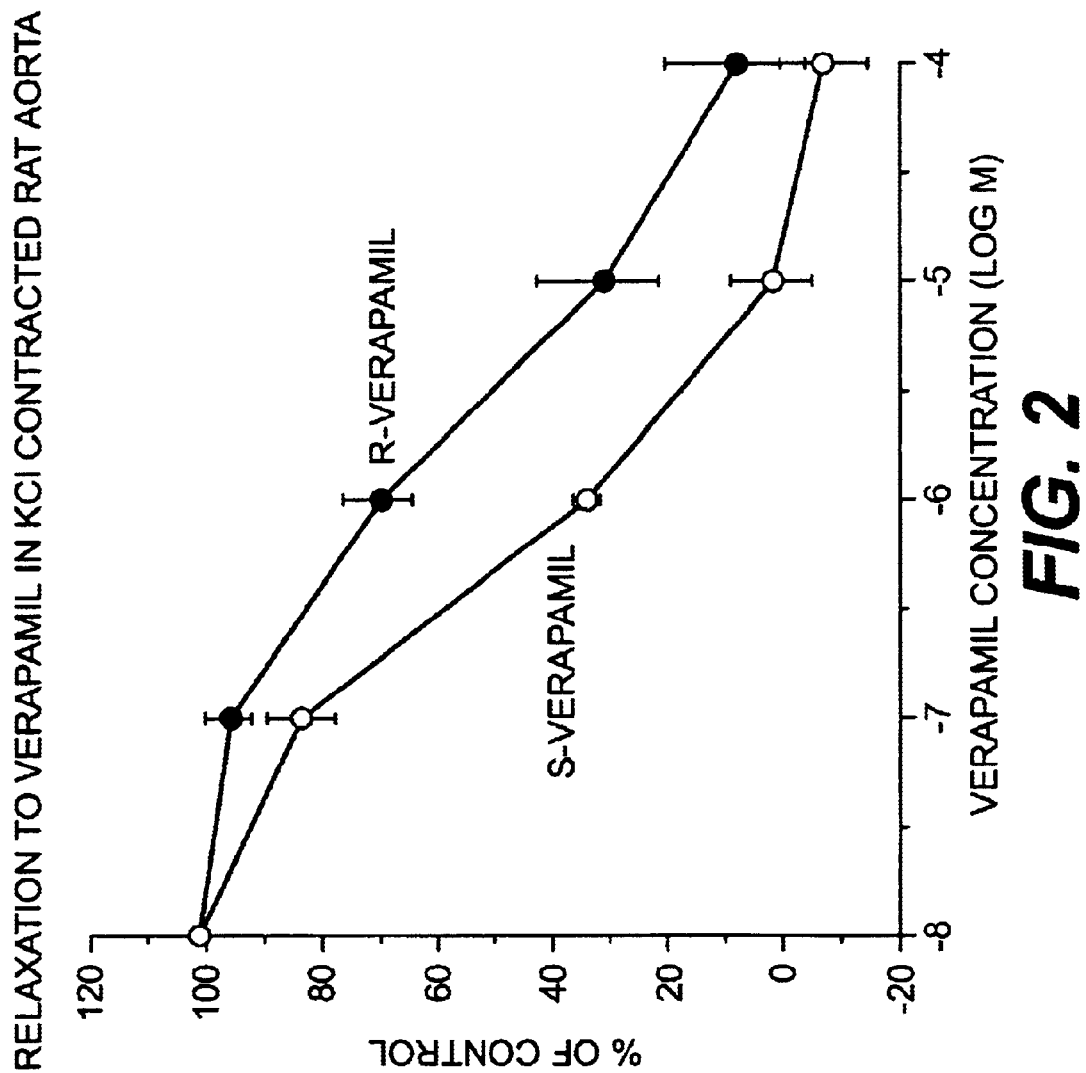
FIG. 2 illustrates the relaxation achieved by (R)-verapamil and (S)-verapamil on KCl-induced contractions in rat aortic tissue.

As shown in FIG. 2, (S)-verapamil ($IC_{50}$ of $4.78 \times 10^{-7}$) was approximately 10 times more potent than (R)-verapamil ($IC_{50}$ of $4.47 \times 10^{-6}$) at relaxing the KCl induced contractions. (S)-verapamil yielded a pIC50 (−log M) of 6.32±0.03, while that for (R)-verapamil was only 5.35±0.24 (n=5 each, p<0.05). Thus, (S)-verapamil was significantly more potent in the aorta than (R)-verapamil.

TABLE 1

| Tissue | Measurement | Potency | | |
|---|---|---|---|---|
| | | S Isomer | R Isomer | Nifedipine |
| Colon | pIC$_{50}$ (−log M) | 6.53 | 6.07 | 6.97 |
| | IC$_{50}$ (M) | 2.95 × 10$^{-7}$ | 8.51 × 10$^{-7}$ | 1.07 × 10$^{-7}$ |
| Aorta | pIC$_{50}$ (−log M) | 6.32 | 5.35 | 7.61 |
| | IC$_{50}$ (M) | 4.78 × 10$^{-7}$ | 4.47 × 10$^{-6}$ | 2.45 × 10$^{-8}$ |
| Intestinal Selectivity Index (IC$_{50}$ Aorta)/(IC$_{50}$ Colon) | | 1.62 | 5.25 | 0.23 |

Example 3
Comparison of Relative Potencies of (R)-Verapamil, (S)-Verapamil, and Nifedipine (R)-verapamil, (S)-verapamil, and Nifedipine all inhibited KCl contractions in rat colon and aorta. While not wishing to be bound by any particular theory, it is possible that these compounds relax the KCl contractions, at least in part, by their calcium channel blocking activity.

Table 1 shows the relative potencies of (R)-verapamil, (S)-verapamil, and nifedipine in the aorta and colon. For each compound, a relative intestinal selectivity index was determined by dividing the IC$_{50}$ observed in the aorta by the IC$_{50}$ observed in the colon. An intestinal selectivity index greater than 1.0 indicates that the compound is more selective for the colon than the aorta. The higher the index number, the greater the intestinal selectivity. An intestinal selectivity index below 1.0 indicates that the compound is more selective for the aorta than the colon.

Nifedipine was significantly more potent in the aorta (IC$_{50}$ of 1.07×10$^{-7}$ M; pIC50 of 7.61±0.11, n=7) than in the colon (IC$_{50}$ of 2.45×10$^{-8}$ M; pIC50 of 6.97±0.25, n=5). The intestinal selectivity of nifedipine was 0.23 (1.07×10$^{-7}$/2.45×10$^{-8}$). Thus, nifedipine was significantly more selective for the aorta than for the colon.

(S)-verapamil was approximately equipotent in the aorta and colon. The IC$_{50}$ of (S)-verapamil in the colon was 2.95×10$^{-7}$ M; in the aorta, the IC$_{50}$ was 4.78×10$^{-7}$ M. Thus, (S)-verapamil yielded an intestinal selectivity of index of 1.62 (4.78×10$^{-7}$/2.95×10$^{-7}$). The pIC50 Values of (S)-verapamil in the colon and aorta were 6.32±0.03 (n=5) and 6.53±0.13 (n=7), respectively.

(R)-verapamil, however, was significantly more potent in the colon than it was in the aorta. The IC$_{50}$ of (R)-verapamil in the colon was 8.51×10$^{-7}$ M; in the aorta, the IC$_{50}$ was 4.78×10$^{-6}$ M. Thus, (R)-verapamil yielded a relatively high intestinal selectivity of index of 5.63 (8.51×10$^{-7}$/4.78×10$^{-7}$). The pIC50 values of (R)-verapamil in the colon and aorta were 6.07±0.16 (n=7) and 5.35±0.24 (n=5), respectively. Thus, given the high intestinal selectivity index, (R)-verapamil is significantly more selective for the intestine than the aorta.

These results show that (S)-verapamil is not selective for the aorta or colon (i.e., it is about equally active in both tissues), while nifedipine exhibits significant aortic-selectivity. In contrast, (R)-verapamil (IC$_{50}$ of 4.47×10$^{-6}$) was 10 times less potent in the aorta than (S)-verapamil (IC$_{50}$ of 4.78×10$^{-7}$), but only three times less potent in the intestine (IC$_{50}$ of 8.51×10$^{-7}$ for (R)-verapamil; IC$_{50}$ of 2.95×10$^{-7}$ for (S)-verapamil). This suggests that the activity of (R)-verapamil is intestinal-selective.

The consequence of this difference in selectivity is that administration of (R)-verapamil can achieve appreciable gastrointestinal effects while avoiding or reducing the disadvantageous cardiovascular effects normally associated with administration of (S)-verapamil and the racemic mixture of verapamil. The S isomer, if dosed at similar levels, would likely produce similar gastrointestinal effects, but also greater cardiovascular effects. The significant cardiovascular effects of the S isomer limits its usefulness in treating, preventing, and/or managing abnormal gastrointestinal motility and intestinal conditions that cause the same. (R)-verapamil, due to its relative intestinal selectivity, overcomes these limitations. As a result, (R)-verapamil can be used to treat, prevent, and/or manage abnormal increases in gastrointestinal motility, and the intestinal conditions that cause the same, due to its greater intestinal-selectivity, while minimizing unwanted cardiovascular effects.

Example 4
Production of an Instant-Release Tablet Formulation of (R)-Verapamil Using Direct Compression

| Ingredient | FUNCTION | Qty % (w/w) |
|---|---|---|
| (R)-VERAPAMIL | Active | 10.00 |
| LACTOSE | Diluent | 55.78 |
| AVICEL ™ PH101 | Dry Binder/diluent | 23.52 |
| SODIUM STARCH GLYCOLATE (EXPLOTAB ™) | Disintegrant | 10.00 |
| COLLOIDAL SILICON DIOXIDE | Glidant | 0.20 |
| MAGNESIUM STEARATE | Lubricant | 0.50 |
| TOTAL | | 100 |

Each of the above-listed ingredients is weighed. The lactose, (R)-verapamil, sodium starch glycolate, colloidal silicon dioxide, and Avicel™, are mixed together in a blender for 15 minutes, until homogeneous. The magnesium stearate is added and the composition is mixed for an additional 5 minutes. The resulting mixture is compressed into oval tablets at a target weight of 400 mg on a suitable tablet machine.

Example 5
Production of an Instant-Release Tablet Formulation of (R)-Verapamil Using Wet Granulation

| Ingredient | FUNCTION | Qty % (w/w) |
|---|---|---|
| (R)-VERAPAMIL | Active | 10.00 |
| LACTOSE | Diluent | 45.28 |
| AVICEL ™ PH101 | Dry Binder/diluent | 29.02 |
| SODIUM STARCH GLYCOLATE (EXPLOTAB ™) | Disintegrant | 10.00 |
| COLLOIDAL SILICON DIOXIDE | Glidant | 0.20 |
| MAGNESIUM STEARATE | Lubricant | 0.50 |
| POLYVINYL PYRROLIDONE | Binder | 5.00 |

-continued

| Ingredient | FUNCTION | Qty % (w/w) |
|---|---|---|
| (PVP) | | |
| *ISOPROPYL ALCOHOL (IPA) | Solvent | N/A |
| TOTAL | | 100 |

*Removed during processing.

Each of the above-listed ingredients is weighed. The PVP is dissolved in the IPA to form a PVP solution. The (R)-verapamil is mixed with 50% of the Avicel™ and 50% of the lactose in a suitable mixer (e.g., Planetary (Hobart), High Shear (Diosna/Fielder)) for 15 minutes to produce a homogenous mixture. While continuing to mix, the granulating fluid (PVP Solution) is added. This composition or mixture is mixed until a desired granulation end point is achieved (add more IPA if needed to produce a suitable granule). The granules are dried with suitable drying equipment (e.g., oven or fluidization equipment) until an acceptable level of moisture (e.g., <1.0%) and IPA (e.g., <0.5%) is achieved.

The dry granulate is then passed through suitable comminution equipment (e.g., Co-Mill, Fitzpatrick mill) fitted with a suitable sized screen (100–500 micron). The granulate is mixed with the colloidal silicon dioxide, sodium starch glycolate, and the remainder of the lactose and Avicel™ in a blender for 15 minutes. The magnesium stearate is added, and mixed for an additional 5 minutes. The resulting mixture is compressed into oval shaped tablets to a target weight of 400 mg on a suitable tablet machine.

Example 6

Production of Modified-Release Tablet Formulations of (R)-Verapamil With Varying Amounts and Grades of Methocel™ using Wet Granulation

| Ingredient | FUNCTION | Qty % (w/w) | Qty % (w/w) | Qty % (w/w) |
|---|---|---|---|---|
| (R)-VERAPAMIL | Active | 30.0 | 30.00 | 30.00 |
| LACTOSE | Diluent | 20.58 | 10.78 | — |
| AVICEL ™ PH101 | Dry Binder diluent | 23.72 | 18.52 | 4.30 |
| METHOCEL ™ | Controlled Release Polymer | 20.00 | 40.00 | 60.00 |
| COLLOIDAL SILICON DIOXIDE | Glidant | 0.20 | 0.20 | 0.20 |
| MAGNESIUM STEARATE | Lubricant | 0.50 | 0.50 | 0.50 |
| POLYVINYL PYRROLIDONE (PVP) | Binder | 5.0 | 5.0 | 5.0 |
| *ISOPROPYL ALCOHOL (IPA) | Solvent | N/A | N/A | N/A |
| TOTAL | | 100 | 100 | 100 |

*Removed during processing.

Each of the above-listed ingredients is weighed. The PVP is dissolved in the IPA to form a PVP solution. The (R)-verapamil is mixed with the Methocel™, 50% of the Avicel™, and 50% of the lactose in a suitable mixer (e.g., Planetary (Hobart), High Shear (Diosna/Fielder)) for 15 minutes to produce a homogenous mixture. The Methocel™ can be substituted with various grades, such as the K and/or E Series, as described by the manufacturer (Dow Chemicals). While continuing to mix, the granulating fluid (PVP Solution) is added. This combination is mixed until a desired granulation end point is achieved (add more IPA if needed to produce a suitable granule). The granules are dried with suitable drying equipment (e.g., oven or fluidization equipment) until an acceptable level of moisture (e.g., <1.0%) and IPA (e.g., <0.5%) is achieved.

The dry granulate is then passed through suitable comminution equipment (e.g., Co-Mill, Fitzpatrick mill) fitted with a suitable sized screen (100–500 micron). The granulate is mixed with the colloidal silicon dioxide, sodium starch glycolate, and the remainder of the lactose and Avicel™ in a blender for 15 minutes. The magnesium stearate is added, and the mixture is mixed for an additional 5 minutes. The resulting mixture is compressed into oval shaped tablets to a target weight of 400 mg on a suitable tablet machine.

Example 7

Production of Instant-Release Drug Loaded Multiparticulate Formulations of (R)-Verapamil

| Ingredient | FUNCTION | Qty (mg/g) |
|---|---|---|
| (R)-VERAPAMIL | Active | 400.00 |
| NON PAREIL SEEDS | Inert carrier | 400.00 |
| POLYVINYL PYRROLIDONE (PVP) | Binder | 50.00 |
| TALC | Antiadherent | 125.0 |
| COLLOIDAL SILICON DIOXIDE | Glidant | 25.00 |
| WATER | Solvent | N/A |
| TOTAL | | 1000 |

The (R)-verapamil, binder, glidant, and antiadherent are dissolved and/or suspended in water. The solution suspension is then sprayed on to the nonpareil seeds using an appropriate fluidized coating machine (e.g., Glatt apparatus). After the solution suspension has been applied to the nonpareil seeds, the drug-loaded instant-release multiparticulates are dried in the fluidized coating machine.

The drug-loaded instant-release multiparticulates may then be formulated into a suitable dosage form, such as gelatin capsules, and/or further processed into a modified-release formulation, as described below. In addition, the drug loaded instant release multiparticulates may be used alone, or in combination with the modified-release multiparticulates described in Example 8, depending on the release profile that is desired.

Example 8

Production of a Modified-Release Multiparticulate Formulation of (R)-Verapamil

Instant-release drug-loaded multiparticulates of (R)-verapamil are prepared, as described above. The multiparticulates are then coated with polymer solution A or B, as follows, to produce a modified-release multiparticulate formulation.

Polymer Solution A

| Ingredient | FUNCTION | Batch (g) |
|---|---|---|
| EUDRAGIT ™ RS 30D | Controlled Release Polymer | 200.00 |
| TALC | Antiadherent | 60.00 |
| TRIETHYL CITRATE | Plasticizer | 12.00 |
| SIMETHICONE EMULSION | Dispersant | 1.00 |
| WATER | Solvent | 392.00 |
| TOTAL | | 665.00 |

Polymer Solution B

| Ingredient | FUNCTION | Batch (g) |
|---|---|---|
| EUDRAGIT ™ RS 12.5 | Controlled Release Polymer | 900.00 |
| EUDRAGIT ™ RL 12.5 | Controlled Release Polymer | 300.00 |
| TALC | Antiadherent | 105.00 |
| DIBUTYL SEBECATE | Plasticizer | 15.00 |
| MAGNESIUM STEARATE | Antiadherant | 30.00 |
| ACETONE | Solvent | 825.00 |
| ISOPROPYL ALCOHOL (IPA) | Solvent | 825 |
| TOTAL | | 3000.00 |

The above listed ingredients in each table are mixed to produce polymer solutions A and B, respectively.

| Ingredient | FUNCTION | Batch (g) | Batch (g) | Batch (g) |
|---|---|---|---|---|
| (R)-VERAPAMIL Drug-Loaded Instant-Release Multiparticulates | Active agent with carrier and excipients | 1000 | 1000 | 1000 |
| *Polymer Solution A or B | Controlled Release Polymer | 50 | 100 | 200 |
| TOTAL | | 1050 | 1100 | 1200 |

*Represents the amount of solid content in polymer solution A or B as the water is removed during processing. The amount of solids applied can be adjusted depending on the type of dissolution profile that is required. Increased amounts of polymer solids will produce decreasing dissolution profiles.

The drug-loaded instant-release mutiparticulates are placed in a suitable fluidized coating machine (e.g., Glatt apparatus). The polymer solution (polymer solution A or B) is then sprayed onto the drug-loaded instant-release multiparticulates in the amounts indicated above. After the required amount of polymer solution has been applied, the polymer-coated multiparticulates are dried in the fluidized coating machine. The resulting modified-release multiparticulates are encapsulated into a hard gelatin capsule using an automated encapsulation machine, in an amount sufficient to produce a 30, 60, 120, 240, or 480 mg dose of (R)-verapamil in each capsule.

Alternatively, the drug-loaded modified-release multiparticulates may be mixed with the drug-loaded instant-release multiparticulates described in Example 7, prior to encapsulation, to vary the rate of release of (R)-verapamil upon administration to a patient.

Example 9

Activity of (R)-Verapamil and (S)-Verapamil in the Vas Deferens

In rat vas deferens there are two components to nerve stimulation, an alpha-nonadrenergic component, dominant in the epididymal portion, and a non-adrenergic (purinergic) component, dominant in the prostatic portion. The latter is blocked by nifedipine. A combination of adrenergic blockade and nifedipine virtually abolishes all components. (Brown et al., Br J Pharmacol., 79:379–393, 1983). FIG. 3 shows that, in contrast to nifedipine (0.1–10 $\mu$M), neither (R)-verapamil nor (S)-verapamil abolished contractions to electrical stimulation in vas prostatic tissue. In the epididymal portion, a combination of alpha adrenergic blockade and nifedipine virtually abolishes all components. FIG. 3 shows that high concentrations of both (R)-verapamil and (S)-verapamil reduced this epididymal contraction (in the presence of nifedipine). (R)- and (S)-verapamil were approximately equipotent. Additional, non-stereospecific properties of verapamil may explain this action, such as alpha-1-adrenoceptor antagonism or prejunctional inhibition of neurotransmission (see, e.g., Motulsky et al., *Circ. Res.*, 52(2): 226–31, 1983.

Example 10

Activity of Other Compounds in the Colon

Other compounds were tested for their ability to relax the KCl contractions, or block the relaxing action of verapamil. Minoxidil (a potassium channel opener) did not relax the KCl contractions. Glibenclamine (a potassium channel blocker) did not block the verapamil-induced relaxations of the KCl contractions. Prazosin (an alpha1-adrenoreceptor antagonist) did not significantly relax KCl contractions. Xylazine (an alpha2-adrenoreceptor agonist) achieved a small relaxation of the contractions, but only at the highest concentration tested ($10^{-4}$M). Nifedipine (a dihydropyridine calcium antagonist) relaxed the KCl contracted colon tissue with a pIC50 (−log M) of 6.97±0.25 (n=5).

What is claimed is:

1. A method for treating an increase in gastrointestinal motility in a subject in need of said method; comprising administering a therapeutically effective amount of enriched (R)-verapamil, or a pharmaceutically acceptable salt thereof, to said subject, wherein the (R)-verapamil is at least about 98% enriched with respect to its (S) stereoisomer.

2. The method of claim 1, wherein the subject is suffering from irritable bowel syndrome (IBS), an infectious disease of the small or large intestine, or symptoms of any of the foregoing.

3. The method of claim 2, wherein the subject is suffering from irritable bowel syndrome.

4. The method of claim 1, wherein the enriched (R)-verapamil is provided in a pharmaceutical formulation.

5. The method of claim 4, the enriched (R)-verapamil formulation is a solid dosage form.

6. The method of claim 4, the enriched (R)-verapamil formulation is administered orally, nasally, rectally, intravaginally, parenterally, buccally, sublingually or topically.

7. The method of claim 6, the enriched (R)-verapamil formulation is administered rectally or orally.

8. The method of claim 4, wherein the enriched (R)-verapamil formulation is provided as a tablet, capsule, or suppository.

9. The method of claim 4, wherein the enriched (R)-verapamil formulation comprises one or more pharmaceutically acceptable excipients.

10. The method of claim 9, wherein the excipient is starch, sugar, cellulose, diluent, granulating agent, lubricant, binder, disintegrating agent, wetting agent, emulsifier, coloring agent, release agent, coating agent, sweetening agent, flavoring agent, perfuming agent, preservative, antioxidant, plasticizer, gelling agent, thickener, hardener, setting agent, suspending agent, surfactant, humectant, carrier, stabilizer, or a combination thereof.

11. The method of claim 1, the enriched (R)-verapamil is administered from one to five times per day.

12. The method of claim 11, wherein the enriched (R)-verapamil is administered one time per day.

13. The method of claim 1, wherein the subject is a human.

14. The method of claim 7, wherein the enriched (R)-verapamil is administered orally and the amount of enriched (R)-verapamil ranges from about 30 mg to about 600 mg per day.

15. The method of claim 14, wherein the amount of enriched (R)-verapamil administered ranges from about 60 mg to about 480 m per day.

16. The method of claim 4, wherein the formulation further comprises one or more additional pharmaceutically active compounds.

17. The method of claim 1, wherein the enriched (R)-verapamil is further administered in combination with one or more additional pharmaceutically active compounds.

18. The method of claim 1, wherein the enriched (R)-verapamil is provided in a modified-release formulation.

19. The method of claim 18, wherein the modified-release formulation comprises one or more water-soluble polymers, water-insoluble polymers, or a combination thereof.

20. The method of claim 19, wherein the water-soluble polymer is chosen from polyvinyl alcohol, polyvinylpyrrolidone, methylcellulose, hydroxypropylcellulose, hydroxypropylmethylcellulose, polyethylene glycol, and mixtures thereof.

21. The method of claim 19, wherein the water-insoluble polymer is chosen from ethylcellulose, cellulose acetate cellulose propionate cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride) or polyurethane, and mixtures thereof.

22. The method of claim 18, wherein the modified-release formulation is an osmotic pump dosage form.

23. The method of claim 18, wherein the modified-release formulation is a matrix system dosage form.

24. The method of claim 18, wherein the modified-release formulation is a membrane controlled dosage form.

25. The method of claim 18, wherein the modified-release formulation comprises a functional coating.

26. The method of claim 18, wherein the modified-release formulation is provided in the form of a caplet, capsule, bead, granule, particle for suspension prior to dosing, sachet, or tablet.

27. A method for preventing an increase in gastrointestinal motility in a subject in need of said method; comprising administering a therapeutically effective amount of enriched (R)-verapamil, or a pharmaceutically acceptable salt thereof, to said subject wherein the (R)-verapamil is at least about 98% enriched with respect to its (S) stereoisomer.

28. A method for managing an increase; in gastrointestinal motility in a subject in need of said method; comprising administering a therapeutically effective amount of enriched (R)-verapamil, or a pharmaceutically acceptable salt thereof, to said subject, wherein the (R)-verapamil is at least about 98% enriched with respect to its (S) stereoisomer.

29. A method for reducing an increase; in gastrointestinal motility in a subject in need of said method comprising administering a therapeutically effective amount of enriched (R)-verapamil, or a pharmaceutically acceptable salt thereof, to said subject, wherein the (R)-verapamil is at least about 98% enriched with respect to its (S) stereoisomer.

* * * * *

UNITED STATES PATENT AND TRADEMARK OFFICE
CERTIFICATE OF CORRECTION

PATENT NO. : 6,849,661 B2
DATED : February 1, 2005
INVENTOR(S) : Kelly et al.

It is certified that error appears in the above-identified patent and that said Letters Patent is hereby corrected as shown below:

Column 26,
Line 47, "method; comprising" should read -- method comprising --.
Lines 60 and 62, "claim 4, the" should read -- claim 4, wherein the --.
Line 66, "claim 6, the" should read -- claim 6, wherein the --.

Column 27,
Line 7, "is starch" should read -- is a starch --.
Line 15, "claim 1, the" should read -- claim 1, wherein the --.
Line 27, "480 m" should read -- 480 mg --.

Column 27, line 45 to column 28, line 1,
"polymer is chosen from ethylcellulose, cellulose acetate cellulose propionate cellulose acetate propionate, cellulose" should read -- polymer is chosen from ethylcellulose, cellulose acetate, cellulose propionate, cellulose acetate propionate, cellulose --.

Column 28,
Lines 27 and 33, "method; comprising" should read -- method comprising --.
Line 30, "subject wherein" should read -- subject, wherein --.
Lines 32 and 38, "increase; in" should read -- increase in --.

Signed and Sealed this

Twenty-sixth Day of April, 2005

JON W. DUDAS
*Director of the United States Patent and Trademark Office*